US00PP21182P3

(12) United States Plant Patent

Alamo et al.

(10) Patent No.: US PP21,182 P3

(45) Date of Patent: Aug. 3, 2010

(54) BLUEBERRY PLANT NAMED 'ALBA'

(50) Latin Name: *Vaccinium corymbosum L.*
Varietal Denomination: Alba

(75) Inventors: Antonio Abad Alamo, Huelva (ES); José Ulf Hayler López, Huelva (ES); Paul M. Lyrene, Micanopy, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/289,062

(22) Filed: Oct. 20, 2008

(65) Prior Publication Data

US 2009/0210980 P1 Aug. 20, 2009

(30) Foreign Application Priority Data

Feb. 14, 2008 (QZ) ..... PBR 2008/0344

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu

(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit at mid-season. The attractive firm light blue flattened-round berries exhibit a pleasant acid blueberry flavor. The plant commonly requires cross pollination, and displays a generally upright growth habit with attractive evergreen foliage. A low chilling requirement is also exhibited.

5 Drawing Sheets

Botanical/commercial classification: *Vaccinium corymbosum* L./Blueberry Plant.

Varietal denomination: cv. Alba.

SUMMARY OF THE INVENTION

The new Blueberry cultivar of the present invention was the product of controlled artificial pollination carried out in a greenhouse at Greenwood, Fla., U.S.A., wherein two parents were crossed during 1998 which previously had been studied in the hope that they would contribute the desired characteristics. The female parent (i.e., the seed parent) was the unreleased 'FL 95-209B' cultivar (non-patented in the United States). The male parent (i.e., pollen parent) was the unreleased 'FL 97-24' cultivar (non-patented in the United States). The parentage of the new cultivar can be summarized as follows:

'FL 95-209B'×'FL 97-24'.

The seeds resulting from the pollination were shipped to Almonte, Huelva, Spain, where they sown during approximately 1999, small plants were obtained which were physically and biologically different from each other and selective research of the progeny was carried out. Selective study during the spring of 2003 resulted in the identification of a single plant of the new cultivar. This plant initially was designated S03-19-02.

It was found that the new Blueberry plant of the present invention displays the following combination of characteristics:

(a) flowers and forms fruit at mid-season, (b) displays a generally upright growth habit with attractive evergreen foliage, (c) commonly requires cross pollination for a good fruit set and quality, (d) displays a low chilling requirement, and (e) forms in abundance attractive firm light blue flattened-round berries that exhibit a pleasant acid blueberry flavor.

The new cultivar well meets the needs of the horticultural industry and can be grown to advantage for the commercial production of blueberries. The yield time is compact and the berries are well suited for machine harvest.

When the new cultivar of the present invention is compared to the 'FL 95-209B' parental cultivar it is found that the new cultivar displays a considerably lighter fruit coloration and a considerably shorter chilling requirement. More specifically, the new cultivar of the present invention commonly displays a chilling requirement of less than approximately 300 hours while the chilling requirement of the 'FL 95-209B' cultivar commonly is approximately 500 hours. No information is available concerning the characteristics of the 'FL 97-24' male parent. Since the 'FL 97-24' male parent no longer exists, it is impossible for Applicants to obtain comparative information with respect to this parental cultivar.

The new cultivar of the present invention can be distinguished from all other Blueberry cultivars known to its originators. Each plant is unreleased to the public and accordingly is not available to the public for use as a comparative cultivar. When compared to the 'Santa Fe' cultivar (U.S.s Plant Pat. No. 10,788), the 'Santa Fe' cultivar commonly requires a significantly longer chill requirement of approximately 600 hours. When compared to the 'Windor' cultivar (U.S. Plant Pat. No. 12,783), the 'Windor' cultivar commonly displays a shorter growth habit that is more round in configuration. When compared to the 'O'Neal' cultivar (non-patented in the United States), the 'O'Neal' cultivar forms darker blue berries and a longer chill requirement of approximately 500 hours. The new cultivar is less susceptible to Leaf Rust than the 'Blue Crisp' cultivar (U.S. Plant Pat. No. 11,033), and is more susceptible to Stem Blight than the 'Star' cultivar (U.S. Plant Pat. No. 10,675).

The new cultivar has been asexually reproduced by the rooting of cuttings beginning during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Alba'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings, and were being grown outdoors at Almonte, Huelva, Spain.

DETAILED DESCRIPTION

Figure 1:
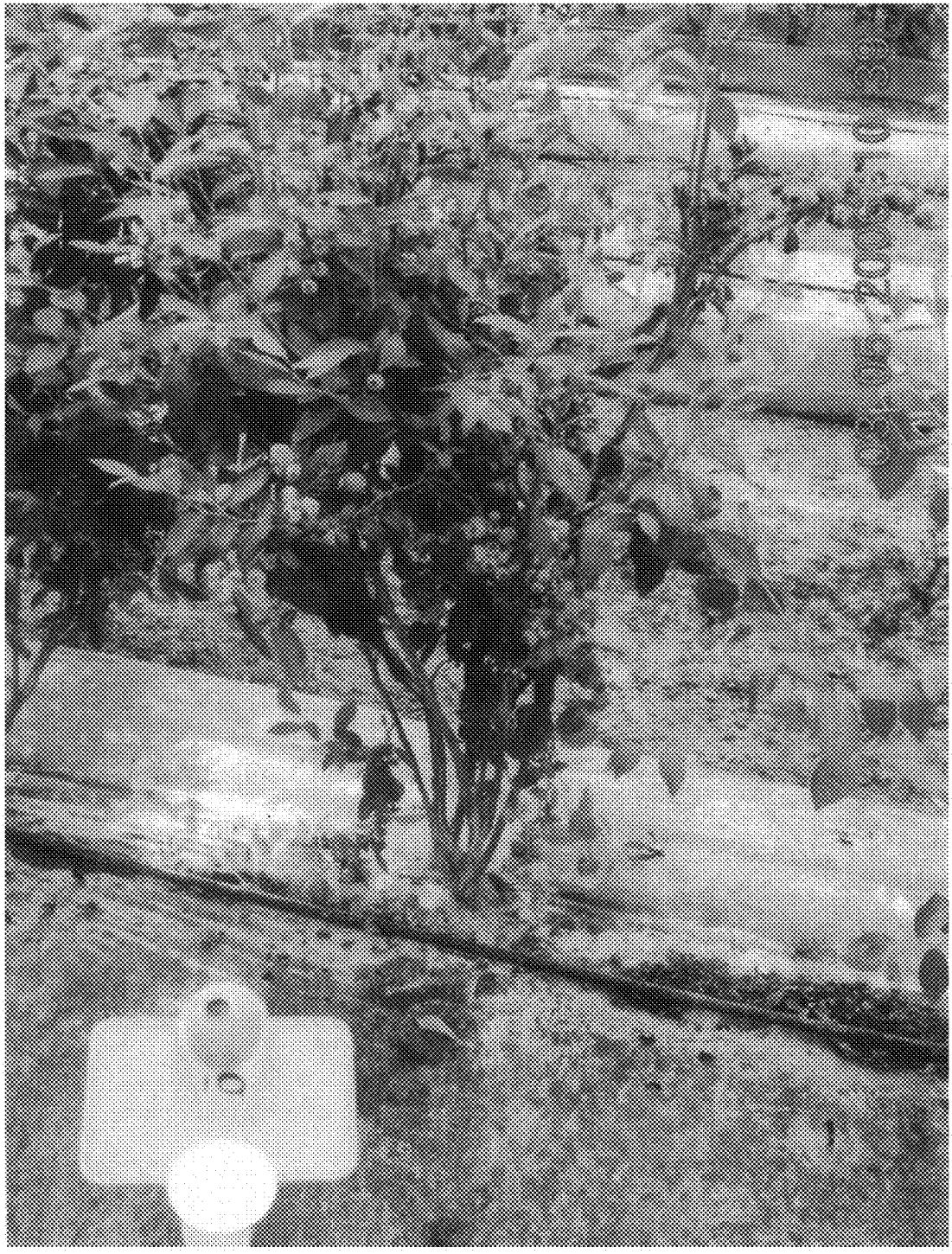
FIG. 1 shows an overall view of a typical fruiting plant of the new cultivar where the generally upright growth habit is illustrated.
Figure 2:
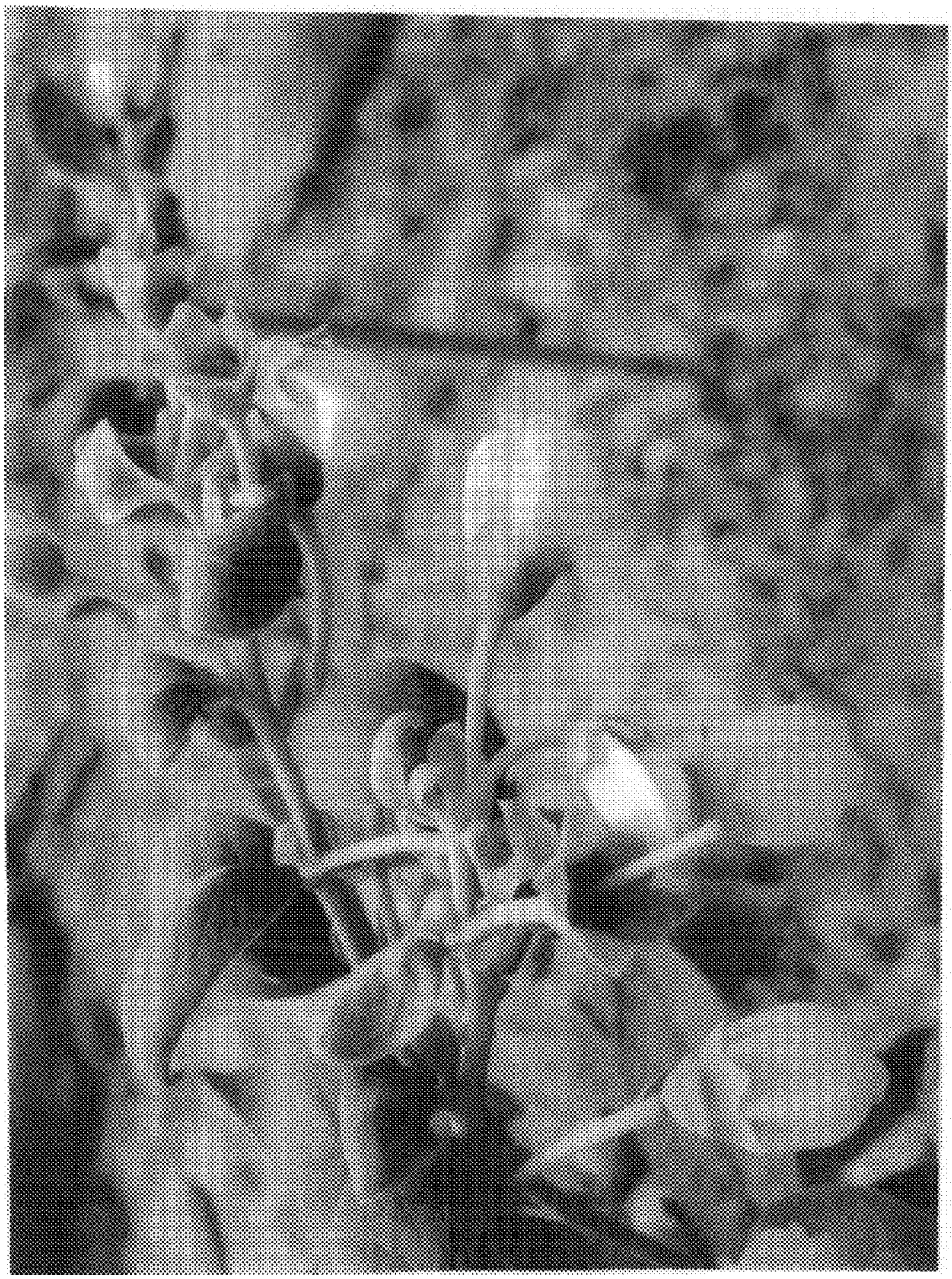
FIG. 2 shows a close view of typical flowers of the new cultivar.
Figure 3:
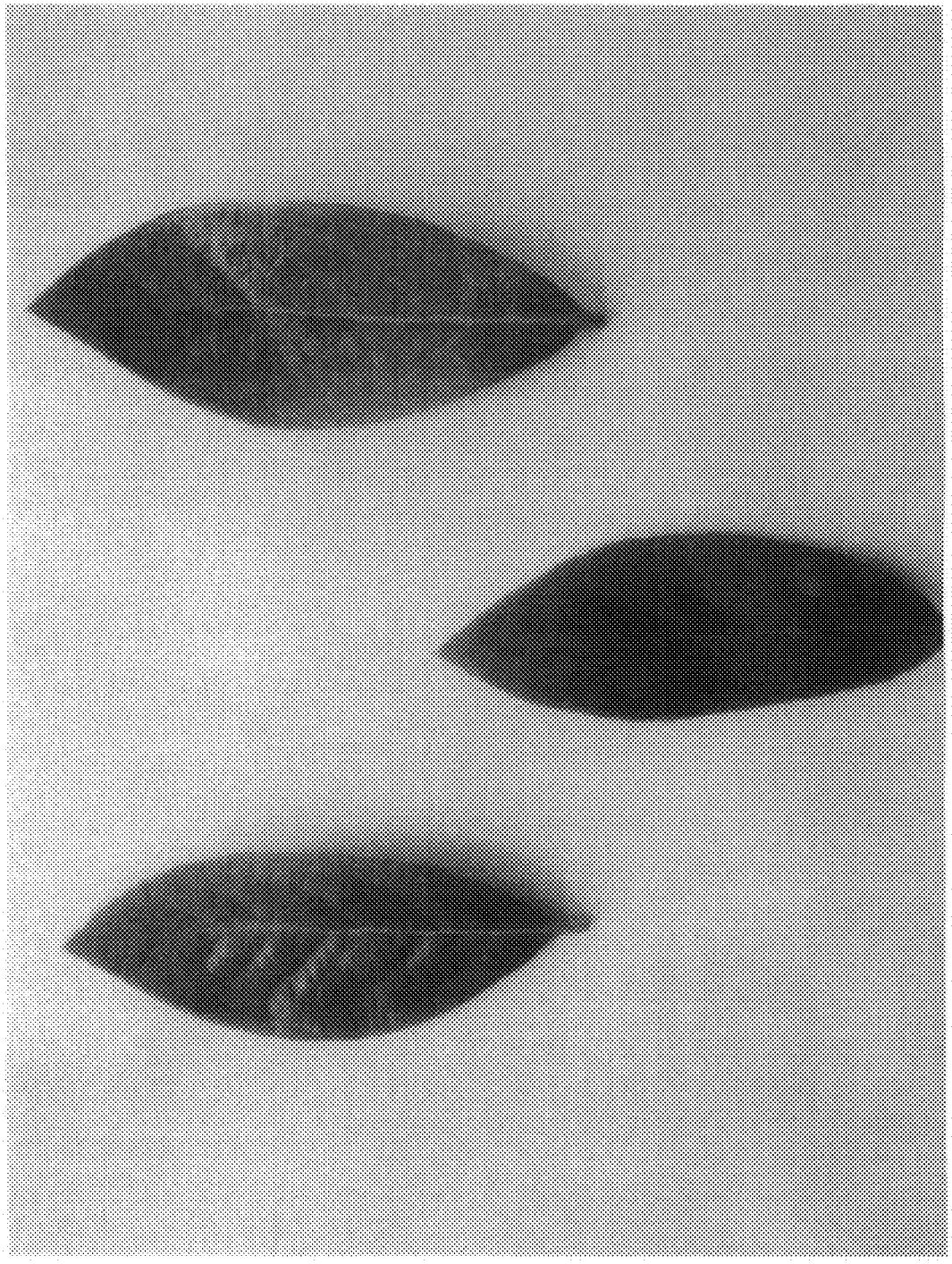
FIG. 3 shows upper (adaxial) surfaces of typical leaves of the new cultivar.
Figure 4:
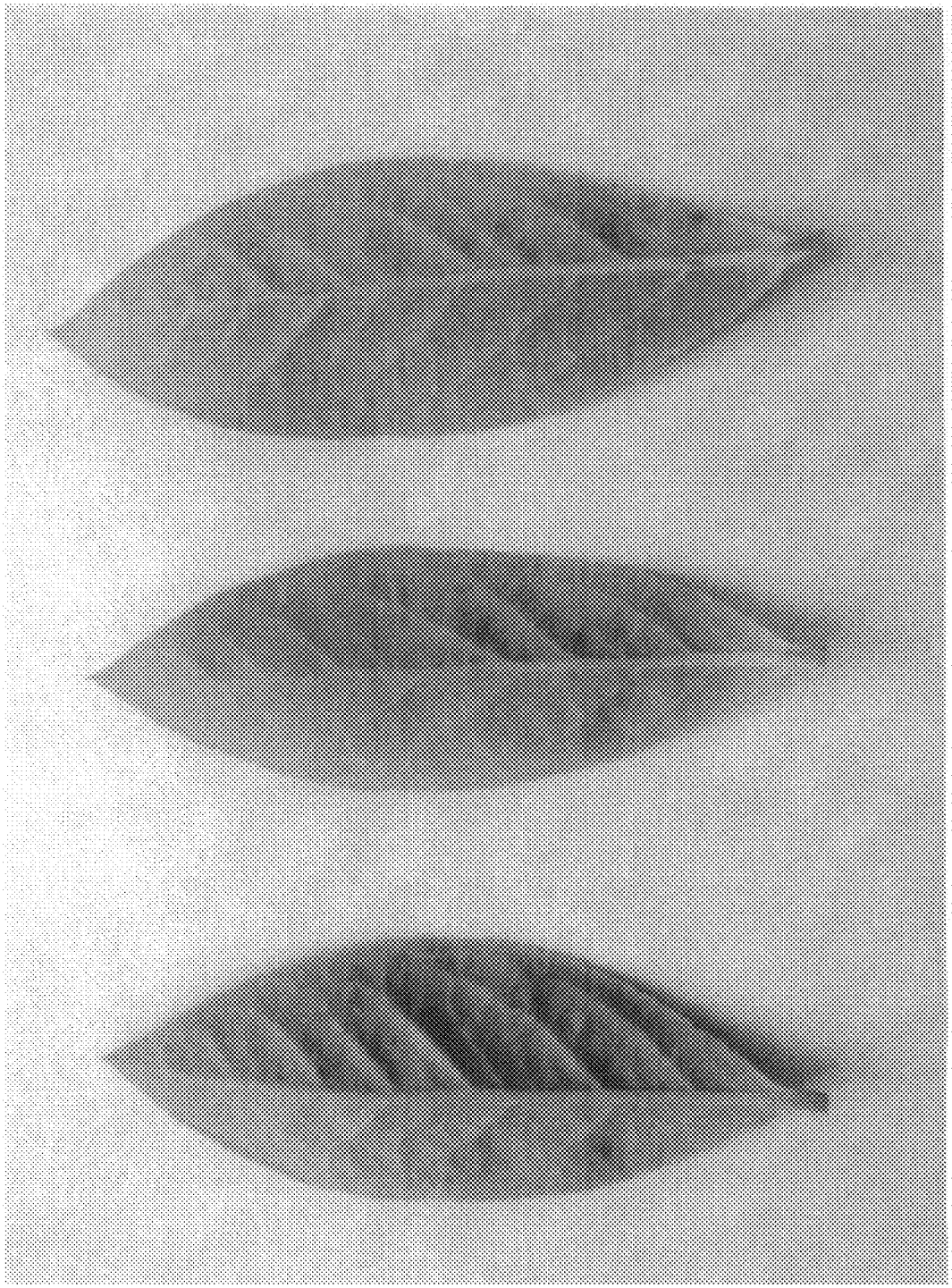
FIG. 4 shows under (abaxial) surfaces of typical leaves of the new cultivar.
Figure 5:
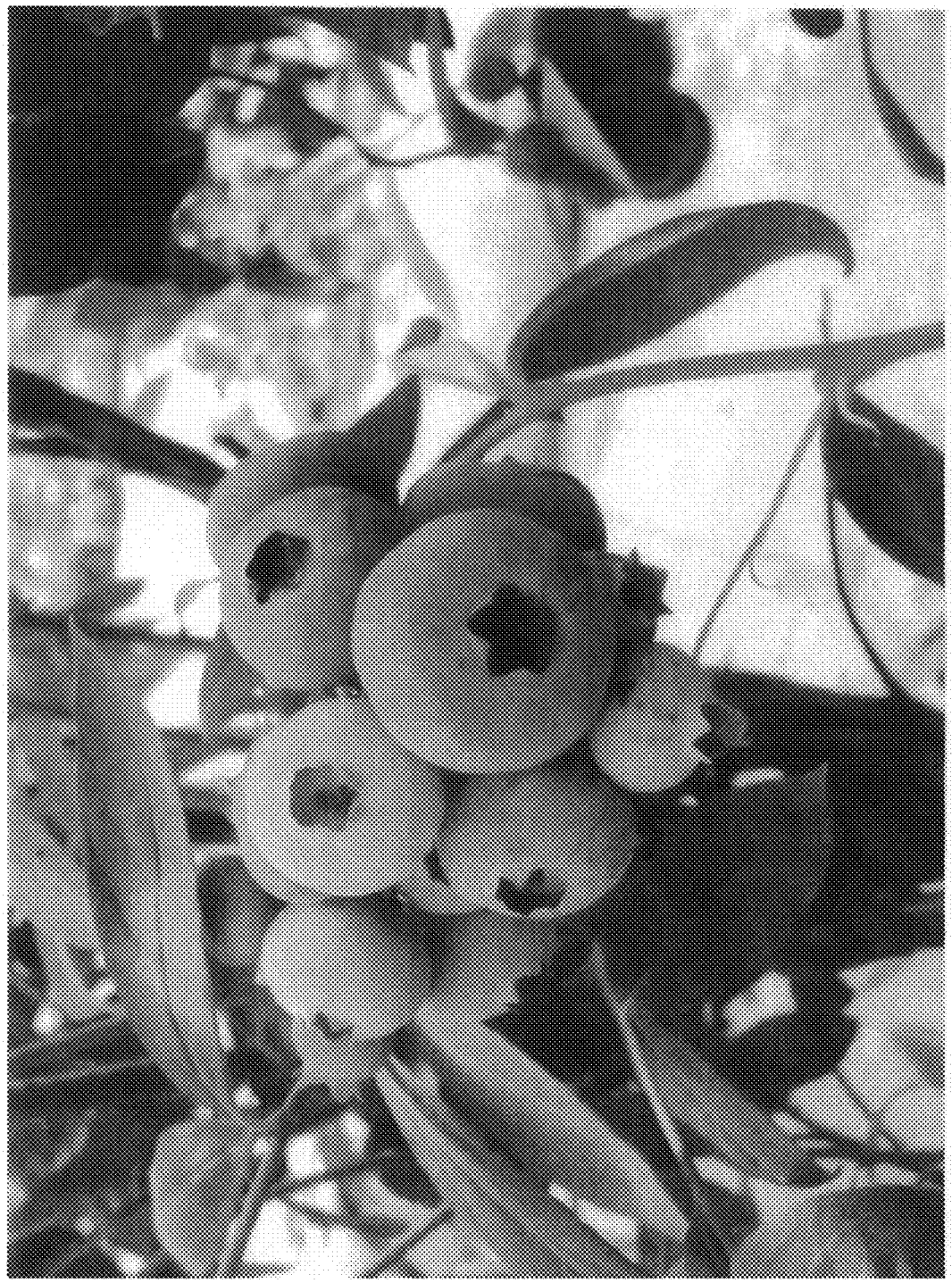
FIG. 5 shows a close view of typical berries of the new cultivar in various stages of development as well as the foliage.

The chart used in the identification of the colors described herein is The R.H.S. Colour Chart of The Royal Horticultural Society, London, England. Ordinary color terms are to be accorded their customary dictionary significance. The description is based on the observation of approximately four-year-old plants of the new cultivar which had been asexually reproduced by the rooting of softwood cuttings while growing outdoors at Almonte, Huelva, Spain.

Plant:

*Growth habit.*—Generally upright.

*Height.*—Approximately 1.6 m at 4 years of age.

*Width.*—Approximately 2.6 m at 4 years of age.

*Mature canes.*—Commonly approximately 42.5 cm in length on average, commonly approximately 2.4 cm in diameter at the base on average, commonly approximately 1.8 cm in diameter towards the tip on average, and near Grey-Brown Group 199D in coloration.

*Foliage retention.*—Evergreen.

*Chill requirement.*—Less than approximately 300 hours, and sometimes less than 250 hours.

Foliage:

*Shape.*—Generally elliptic (as illustrated).

*Length.*—Commonly approximately 61 mm on average.

*Width.*—Commonly approximately 30 mm on average.

*Apex.*—Acute.

*Base.*—Acute.

*Margin.*—Entire.

*Texture.*—Glabrous and non-glandular on both surfaces.

*Color.*—Green Group 137B on the upper (adaxial) surface, and Green Group 138B on the under (abaxial) surface.

*Petiole.*—Commonly approximately 3.3 mm in length on average, commonly approximately 1.6 mm in diameter on average, near Yellow-Green Group 145C in coloration on both surfaces.

Flowers:

*Time.*—Mid-season, at Almonte, Huelva, Spain, with first flower commonly at approximately January 10$^{th}$, and 50 percent bloom at approximately February 10$^{th}$.

*Number.*—Commonly approximately 6 flowers per inflorescence on average.

*Petals.*—5 in number and fused into a corolla tube.

*Corolla shape.*—Urceolate.

*Corolla size.*—The corolla tube commonly is approximately 9.8 mm in length on average, and approximately 8.2 mm in width on average at the widest point.

*Corolla color.*—On open flowers the corolla tube is near White Group 155D, and on closed flowers the corolla tube is near Red-Purple Group 63C.

*Sepals.*—Commonly 5 in number.

*Calyx.*—Commonly approximately 3.6 mm in length on average, a basin depth of approximately 2.8 mm, a basin diameter of approximately 7.7 mm, and a coloration of Green Group 143D.

*Stamen.*—Commonly approximately 10 to 12 in number.

*Filaments.*—Pubescent, commonly approximately 3 mm in length on average, pale-green in coloration, and approximately one- half are adnate with strong connection to the petals.

*Anthers.*—Commonly approximately 5 mm in size on average, bronze-colored, and the size ratio of pollen sac:pollen tube commonly is approximately 2:3.

*Pistil.*—One per flower and light green in coloration.

*Style.*—Cone-shaped, commonly approximately 10.4 mm in length on average, and approximately 0.8 to 1 mm in thickness at the base.

*Peduncle.*—Commonly approximately 8 mm in length, approximately 1.1 mm in diameter, and Yellow-Green Group 144D in coloration commonly with shades of near Greyed-Red Group 179B at the side.

*Fertility.*—Commonly not self-fertile. Representative pollinators include the 'Misty' cultivar (non-patented in the United States), 'Star' cultivar (U.S. Plant Pat. No. 10,675), 'Sharpblue' cultivar (non-patented in the United States), 'Romero' cultivar (U.S. Plant Pat. No. 20,373), 'Rocio' cultivar (U.S.s Plant Pat. No. 20,374), 'Azulema' cultivar (U.S. Plant patent application Ser. No. 12/289,127, filed Oct. 21, 2008), and 'Altair' cultivar (U.S. Plant Pat. No. 20,830).

*Fragrance.*—None.

Fruit:

*Time.*—Commonly from approximately April 20th to May 30$^{th}$ at Almonte, Huelva, Spain (i.e., approximately 6 weeks).

*Shape.*—Generally flattened-round.

*Height.*—Commonly approximately 13 mm on average.

*Width.*—Commonly approximately 19 mm on average.

*Weight.*—Approximately 3.03 g/berry on average when plants were 4 years of age.

*Fruit scar.*—Approximately 1.25 mm in size, and dry.

*Seed number.*—Commonly approximately 17 per berry on average.

*Seed.*—Size commonly approximately 1.1 mm in length and approximately 0.7 mm in width on average.

*Immature color.*—Commonly near Green Group 130D with bloom and Yellow-Green Group 145B without bloom.

*Mature color.*—Light blue, Violet Blue Group 97B to 97C with bloom and Black Group 202A without bloom.

*Flesh color.*—Yellow-Green Group 154D.

*Firmness.*—Medium.

*Productivity.*—Abundant, approximately 3.44 Kg/plant on average when plants were 4 years of age.

*Flavor.*—Displays a pleasant acid blueberry flavor, and commonly displays a level of sweetness of approximately 12.9° Brix.

Development:

*Ability to store.*—The fruit stores well under refrigeration, when stored at 8° C. approximately 95 percent of the berries are of good quality 7 days after harvest, and when stored at 20° C. approximately 75 percent of the berries are of good quality 7 days after harvest.

*Disease tolerance.*—No special sensitivity to common Blueberry diseases. such as Leaf Rust (*Pucciniastrum vaccinii*) and Botrytis (*Botrytis cinerea*) has been encountered during observations to date at Almonte, Huelva, Spain. During observations to date the new cultivar is less susceptible to Leaf Rust than the 'Blue Crisp' cultivar, and is more susceptible to Stem Blight than the 'Star' cultivar.

*Insects.*—Is susceptible to aphids and thrips.

*Cultural conditions.*—Is well suited for evergreen management under tunnels or open-air deciduous management with machine harvest.

*Heat resistance.*—Has withstood temperatures as high as 45° C. at Almonte, Huelva, Spain.

*Cold resistance.*—Has withstood temperatures as low as −10° C. at Almonte, Huelva, Spain.

Plants of the 'Alba' cultivar have not been observed under all possible environmental conditions to date. Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers and forms fruit at mid-season, (b) displays a generally upright growth habit with attractive evergreen foliage, (c) commonly requires cross pollination for good fruit set and quality, (d) displays a low chilling requirement, and (e) forms in abundance attractive firm light blue flattened-round berries that exhibit a pleasant acid blueberry flavor;

substantially as herein shown and described.

* * * * *